United States Patent
Nam

(10) Patent No.: US 8,609,626 B2
(45) Date of Patent: Dec. 17, 2013

(54) NLK AS A MARKER FOR DIAGNOSIS OF LIVER CANCER AND AS A THERAPEUTIC AGENT THEREOF

(75) Inventor: Suk Woo Nam, Seoul (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/637,008

(22) PCT Filed: Mar. 25, 2011

(86) PCT No.: PCT/KR2011/002031
§ 371 (c)(1),
(2), (4) Date: Sep. 24, 2012

(87) PCT Pub. No.: WO2011/118994
PCT Pub. Date: Sep. 29, 2011

(65) Prior Publication Data
US 2013/0065945 A1    Mar. 14, 2013

(30) Foreign Application Priority Data

Mar. 25, 2010 (KR) .................... 10-2010-0026751
Mar. 24, 2011 (KR) .................... 10-2011-0026618

(51) Int. Cl.
*C12N 15/11* (2006.01)
*C12Q 1/68* (2006.01)

(52) U.S. Cl.
USPC ........................................ 514/44 A; 435/6.1

(58) Field of Classification Search
None
See application file for complete search history.

(56) References Cited

PUBLICATIONS

Yasuda et al, Mammalian Nemo-like kinase enhances β-catenin-TCF transcription activity in human osteosarcoma and neuroblastoma cells, 2007, Proc Jpn Acad, Ser. B, 83: 16-25.*
Jung et al, Aberrant regulation of Nemo-like kinase and its disruption elicits regression of tumor cell growth by cyclin D1 and CDK2 suppression in human hepatocellular carcinoma, Sep. 2009, Molecular and Cellular Toxicology, 5, No. 3, Supplement, p. 48.*
Ishitani et al, Nemo-like kinase is involved in NGF-induced neurite outgrowth via phosphorylating MAP1B and paxillin, 2009, Journal of Neurochemistry, 111: 1104-1118).*
Ramaswamy et al, Multiclass cancer diagnosis using tumor gene expression signatures, PNAS, 2001, vol. 98, No. 26, 15149-15154.*
Jun Yasuda et al., "Nemo-like kinase induces apoptosis in DLD-1 human colon cancer cells", Biochemical and Biophysical Research Communications, 2003, pp. 227-233, Elsevier.
Katayoon H. Emami et al., "Nemo-Like Kinase Induces Apoptosis and Inhibits Androgen Receptor Signaling in Prostate Cancer Cells", The Prostate, 2009, pp. 1481-1492, vol. 69.
Junfang Ji et al., "Identification of MicroRNA-181 by Genome-Wide Screening as a Critical Player in EpCAM-Positive Hepatic Cancer Stem Cells", Hepatology, Aug. 2009, pp. 472-480, vol. 50, No. 2.
Kwang Hwa Jung et al., "Targeted Disruption of Nemo-Like Kinase Inhibits Tumor Cell Growth by Simultaneous Suppression of Cyclin D1 and CDK2 in Human Hepatocellular Carcinoma", Journal of Cellular Biochemistry, 2010, pp. 687-696.
International Search Report for PCT/KR2011/002031 filed on Mar. 25, 2011.

* cited by examiner

*Primary Examiner* — Tracy Vivlemore
*Assistant Examiner* — Kate Poliakova

(57) ABSTRACT

A novel marker for diagnosis of liver cancer and use thereof are provided. To be specific, a marker for diagnosis of liver cancer using over-expression of NLK (neuro-like kinase) in liver cancer cell is provided, along with a composition for diagnosis of liver cancer, a kit, a microarray, and a method for diagnosing liver cancer using the marker. Additionally, a method for screening a substance to prevent or treat liver cancer by decreasing expression of the marker gene or protein, and a composition for preventing or treating liver cancer including such substance are provided. Accordingly, the NLK gene can be efficiently used as a target for diagnosis and treatment of liver cancer.

4 Claims, 11 Drawing Sheets

SEQUENCE LISTING

<160> NUMBER OF SEQ ID NOS: 7

<210> SEQ ID NO 1
<211> LENGTH: 1584

```
<212> TYPE: DNA
<213> ORGANISM: Artificial Sequence
<220> FEATURE:
<223> OTHER INFORMATION: NLK gene sequence

<400> SEQUENCE: 1
atgtctcttt gtggcgcaag agccaacgca aaaatgatgg cggcttacaa tggcggtaca      60
tctgcagcag cagcaggtca ccaccaccac catcaccacc accttccaca cctcccctcct    120
cctcacctgc accaccacca ccaccctcaa caccatcttc atccggggtc ggctgccgct    180
gtacaccctg tacagcagca cacctcttcg gcagctgcgg cagccgcagc agcggctgca    240
gctgcagcca tgttaaaccc tgggcaacaa cagccatatt tcccatcacc ggcaccgggg    300
caggctcctg gaccagctgc agcagcccca gctcaggtac aggctgccgc agctgctaca    360
gttaaggcgc accatcatca gcactcgcat catccacagc agcagctgga tattgagccg    420
gatagaccta ttggatatgg agcctttggt gttgtctggt cagtaacaga tccaagagat    480
ggaaagagag tagcgctcaa aaagatgccc aacgtcttcc agaatctggt ctcttgcaaa    540
agggtcttcc gggaattgaa gatgttgtgt tttttaagc atgataatgt actctctgcc     600
cttgacatac tccaacctcc acacattgac tattttgaag aaatatatgt tgtcacagaa    660
ttgatgcaga gtgacctaca taaaattatc gtctctcctc aaccactcag ctcagatcat    720
gtcaaagttt ttctttatca gattttgcga ggtttgaaat atctccattc agctggcatt    780
ttacatcgag acattaagcc agggaatctc cttgtgaaca gcaactgtgt tctaaagatt    840
tgtgattttg gattggccag agtggaagaa ttagatgaat cccgtcatat gactcaggaa    900
gttgttactc agtattatcg ggctccagaa atcctgatgg gcagccgtca ttacagcaat    960
gctattgaca tctggtctgt gggatgtatc tttgcagaac tactaggacg aagaatattg   1020
tttcaggcac agagtcccat tcagcagttg gatttgatca cggatctgtt gggcacacca   1080
tcactggaag caatgaggac agcttgtgaa ggcgctaagg cacatatact cagggtctcc   1140
cataaacagc catctcttcc tgtactctat accctgtcta gccaggctac acatgaagct   1200
gttcatctcc tttgcaggat gttggtcttt gatccatcca aaagaatatc cgctaaggat   1260
gccttagccc accctacct agatgaaggg cgactacgat atcacacatg tatgtgtaaa    1320
tgttgctttt ccacctccac tggaagagtt tataccagtg actttgagcc tgtcaccaat   1380
cccaaatttg atgacacttt cgagaagaac ctcagttctg tccgacaggt taaagaaatt   1440
attcatcagt tcattttgga acagcagaaa ggaaacagag tgcctctctg catcaaccct   1500
cagtctgctg cttttaagag ctttattagt tccactgttg ctcagccatc tgagatgccc   1560
ccatctcctc tggtgtggga gtga                                          1584

<210> SEQ ID NO 2
<211> LENGTH: 19
<212> TYPE: RNA
<213> ORGANISM: Artificial Sequence
<220> FEATURE:
<223> OTHER INFORMATION: nlk sense

<400> SEQUENCE: 2
gggucuuccg ggaauugaa                                                   19

<210> SEQ ID NO 3
<211> LENGTH: 19
<212> TYPE: RNA
<213> ORGANISM: Artificial Sequence
<220> FEATURE:
<223> OTHER INFORMATION: nlk antisense
```

```
<400> SEQUENCE: 3
uucaauuccc ggaagaccc                                                    19

<210> SEQ ID NO 4
<211> LENGTH: 20
<212> TYPE: DNA
<213> ORGANISM: Artificial Sequence
<220> FEATURE:
<223> OTHER INFORMATION: nlk F primer

<400> SEQUENCE: 4
gctggatatt gagccggata                                                   20

<210> SEQ ID NO 5
<211> LENGTH: 20
<212> TYPE: DNA
<213> ORGANISM: Artificial Sequence
<220> FEATURE:
<223> OTHER INFORMATION: nlk R primer

<400> SEQUENCE: 5
catcttcaat tcccggaaga                                                   20

<210> SEQ ID NO 6
<211> LENGTH: 20
<212> TYPE: DNA
<213> ORGANISM: Artificial Sequence
<220> FEATURE:
<223> OTHER INFORMATION: GAPDH F primer

<400> SEQUENCE: 6
accaggtggt ctcctctgac                                                   20

<210> SEQ ID NO 7
<211> LENGTH: 20
<212> TYPE: DNA
<213> ORGANISM: Artificial Sequence
<220> FEATURE:
<223> OTHER INFORMATION: GAPDH R primer

<400> SEQUENCE: 7
tgctgtagcc aaattcgttg                                                   20
```

NLK AS A MARKER FOR DIAGNOSIS OF LIVER CANCER AND AS A THERAPEUTIC AGENT THEREOF

BACKGROUND OF THE INVENTION

1. Field of the Invention

The present invention relates to a novel marker for diagnosis of liver cancer capable of efficiently diagnosing and predicting liver cancer, a diagnosis kit, a microarray, a composition for liver cancer diagnosis, and a method for diagnosing liver cancer using the novel marker for diagnosis of liver cancer, and a composition for preventing or treating liver cancer.

2. Description of the Related Art

Hepatocellular carcinoma (HCC) is the fifth most common cancer responsible for the 0.5 million deaths every year. The survival rate of the HCC patients has not been improved over the past 20 years and the death rate is almost equivalent to the attack rate. Chronic hepatitis developed by the inflammation with hepatitis B virus (HBV) or hepatitis C virus (HCV) and exposure to cancer-triggering aflaxtoxin B1 are known to be the major risk factor regarding HCC.

Further, there is a report that changes in the cell-cycle regulating substances in the transition to G1 phase in the cell cycle mechanism are associated with the formation of liver cancer. It has also been reported that DNA mutation and the genetic alternation are observed in the liver cancer patient's tissue.

The above indicates that it is not a handful of specific genes that causes the liver cancer to initiate, but rather complicated interaction among many genes involved in intracellular signaling and regulation mechanism which are generated as the malignancy of the cancer progresses. Accordingly, a study would be quite limited if it only focuses on the mechanism of formation of liver cancer based on a few specific genes. Accordingly, it is necessary to discover new genes possibly involved with the liver cancer based on comparative analysis of various genes' expression between normal liver cells and hepatoma cell lines.

Recent studies have reported that genetic alterations of tumor associated genes such as p53, β-catenin, and AXIN1 are involved in hepatocarcinogenesis; however, the frequencies of somatic mutations, in these genes, appear o be very low in patients with HCC. Furthermore, it is unclear how these genetic changes precisely cause the clinical characteristics observed in individual patients with HCC. Therefore, the major molecular events underlying HCC remain to be identified.

Accordingly, a novel marker is necessary, which can analyze a cause of liver cancer with increased accuracy, and predict or diagnose a liver cancer.

DETAILED DESCRIPTION OF THE INVENTION

Technical Object

The present inventors confirmed that NLK (nemo-like kinase) expression in HCC tissue is distinguished from that in normal tissue, and further confirmed that when NKL expression is suppressed, it is possible to prevent or treat the liver cancer through inhibition of proliferation of liver cancer cells, and thus completed the present invention.

Accordingly, an object of the present invention is to provide a composition for diagnosing liver cancer using a NLK gene as a marker for diagnosing the liver cancer.

Another object of the present invention is to provide a composition for preventing or treating a liver cancer, comprising oligonucleotide for inhibiting NLK (nemo-like kinase) expression.

Yet another object of the present invention is to provide a method for predicting or diagnosing initiation of liver cancer, comprising a step of measuring expression of NLK (nemo-like kinase) as a liver cancer mark.

Yet another object of the present invention is to provide a method for screening substance for predicting or treating liver cancer.

Yet another object of the present invention is to provide a kit for diagnosing liver cancer and a microarray for diagnosing liver cancer.

Yet another object of the present invention is to provide a method for treating liver cancer, comprising a step of administering oligonucleotide for inhibiting expression of nemo-like kinase (NLK) to a subject in need of the same.

Means to Solve the Object

In order to accomplish the above-mentioned objects, the present invention provides a method for treating liver cancer, comprising a step of administering oligonucleotide for inhibiting expression of nemo-like kinase (NLK) to a subject in need of the same.

In one embodiment, the oligonucleotide is antisense oligonucleotide, siRNA or shRNA regarding a gene encoding NLK (nemo-like kinase).

In one embodiment, the siRNA has a sequence of SEQ ID NO: 2 or SEQ ID NO: 3.

In one embodiment, the oligonucleotide to inhibit expression of the NLK inhibits expression of cyclin D1, CDK2 or beta-catenin, and has anticancer activity by inhibiting progression of cell cycle in G1/S phase.

In one embodiment, the NLK gene has a sequence represented by SEQ ID NO: 1.

In one embodiment, the liver cancer is hepatocellular carcinoma (HCC).

An embodiment of the present invention also provides a method for predicting or diagnosing onset of liver cancer, including steps of (a) measuring expression level of NLK gene or protein level encoded by the gene from a biological sample of a patient with suspected liver cancer, and (b) comparing the expression level of the gene or the level of the protein encoded by the gene with expression level of a corresponding gene or protein level thereof of a normal sample as a control.

In one embodiment, the measuring is selected from a group consisting of reverse transcriptase-polymerase chain reaction, real time-polymerase chain reaction, Western blot analysis, Northern blot analysis, enzyme linked immunosorbent assay (ELISA), radioimmunoassay (RIA), radioimmunodiffusion, and immunoprecipitation assay.

In one embodiment, the measuring the expression level of the NLK gene or the level of the protein encoded by the gene is conducted by using a primer, a probe or an antibody specifically binding to the gene or protein.

An embodiment of the present invention also provides a method for screening a substance for the prevention or treatment of liver cancer, including steps of (a) contacting a sample of interest to a cell comprising NLK (nemo-like kinase) gene or NLK protein, (b) measuring expression level of the NLK gene, amount of NLK protein or activity of NLK protein, and (c) as a result of the measuring at step (b), if the expression level of NLK gene, protein level of NLK or activity of NLK protein is decreased, determining the sample to be a substance for preventing or treating liver cancer.

In one embodiment, the measuring is selected from a group consisting of reverse transcriptase-polymerase chain reaction, real time-polymerase chain reaction, Western blot analysis, Northern blot analysis, enzyme linked immunosorbent assay (ELISA), radioimmunoassay (RIA), radioimmunodiffusion, and immunoprecipitation assay.

An embodiment of the present invention also provides a kit for diagnosis of liver cancer, including mRNA of nemo-like kinase (NLK) or protein level thereof.

In one embodiment, the kit is a PCR kit, a DNA chip kit or a protein chip kit.

In one embodiment, the substance is a primer, a probe or an antibody specifically binding to the NLK gene or protein.

An embodiment of the present invention also provides a microarray for diagnosis of liver cancer, including polynucleotide of nemo-like kinase (NLK) represented by SEQ ID NO: 1.

Effect of the Invention

NLK expression is aberrantly up-regulated in liver cancer marker gene than in normal tissue, suggesting that suppression of the gene causes down-regulation of cyclin D1 and CDK2 expression in the liver cancer cells, so that simultaneous inhibition of cell cycle progression of G1/S phase and cellular proliferation provides effect of prevention or treatment of liver cancer. Accordingly, the NLK gene can be efficiently used as a target for diagnosis and treatment of liver cancer.

BRIEF DESCRIPTION OF THE DRAWINGS

The above and/or other aspects and advantages of the present invention will become apparent and more readily appreciated from the following detailed description, taken in conjunction with the accompanying drawings of which.

BEST MODE

While researching for a novel marker for diagnosing liver cancer at early stage and with accuracy, the present inventors discovered NLK gene which aberrantly up-regulated in HCC or liver cancer tissue than in normal counterpart, and thus confirmed that this can be used as a marker for liver cancer diagnosis.

NLK (neuro-like kinase) is a member of the extracellular-signal regulated kinase/microtubule-associated protein kinase (Erk/MAPKs) and Cdks(cyclin-directed kinases), and TAK1 (transforming growth-factor-b-activated kinase 1) of the MAPKK (MAPK kinase kinase) superfamily is known to as a potential activator of NLK in Wnt signal pathway. Nmo, in *Drosophila* and LIT-1, in *Caenorhabditis elegans*, have been found to be homologous to vertebrate NLK in the genetic studies; they act as regulators of Wnt signaling during the development of the wings in the fly and in the cell division of *C. elegans*. Therefore, NLK/Nmo/LIT-1 has been identified as a very important regulator of cell growth, patterning, and death in a variety of organisms.

To be specific, although the NLK, discovered according to the present invention, is reported to be the tumor suppressor in the Wnt/β-catenin signaling pathway of colon cancer, the other events occurring downstream of NLK pathways in other types of cancer remain unclear.

However, in the present invention, the inventors confirmed that NLK is up-regulated in the HCC, which is quite contradictory to the conventionally-reported role as a tumor suppressor in colorectal cancer.

Figure 1:
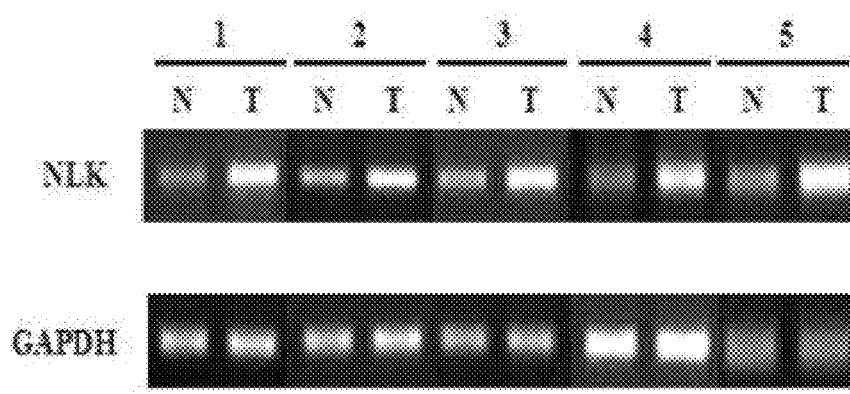
FIG. 1 shows comparison of NLK mRNA expression by RT-PCT regarding human hepatocellular carcinoma (HCC) and normal liver tissue sample.
Figure 1:
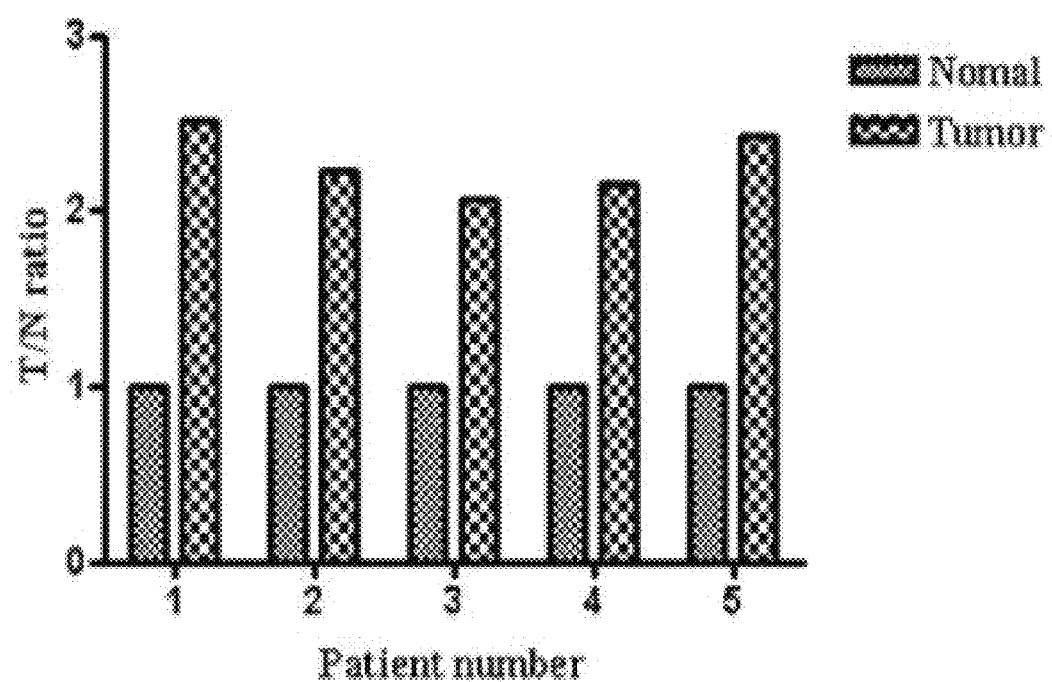
Figure 2:
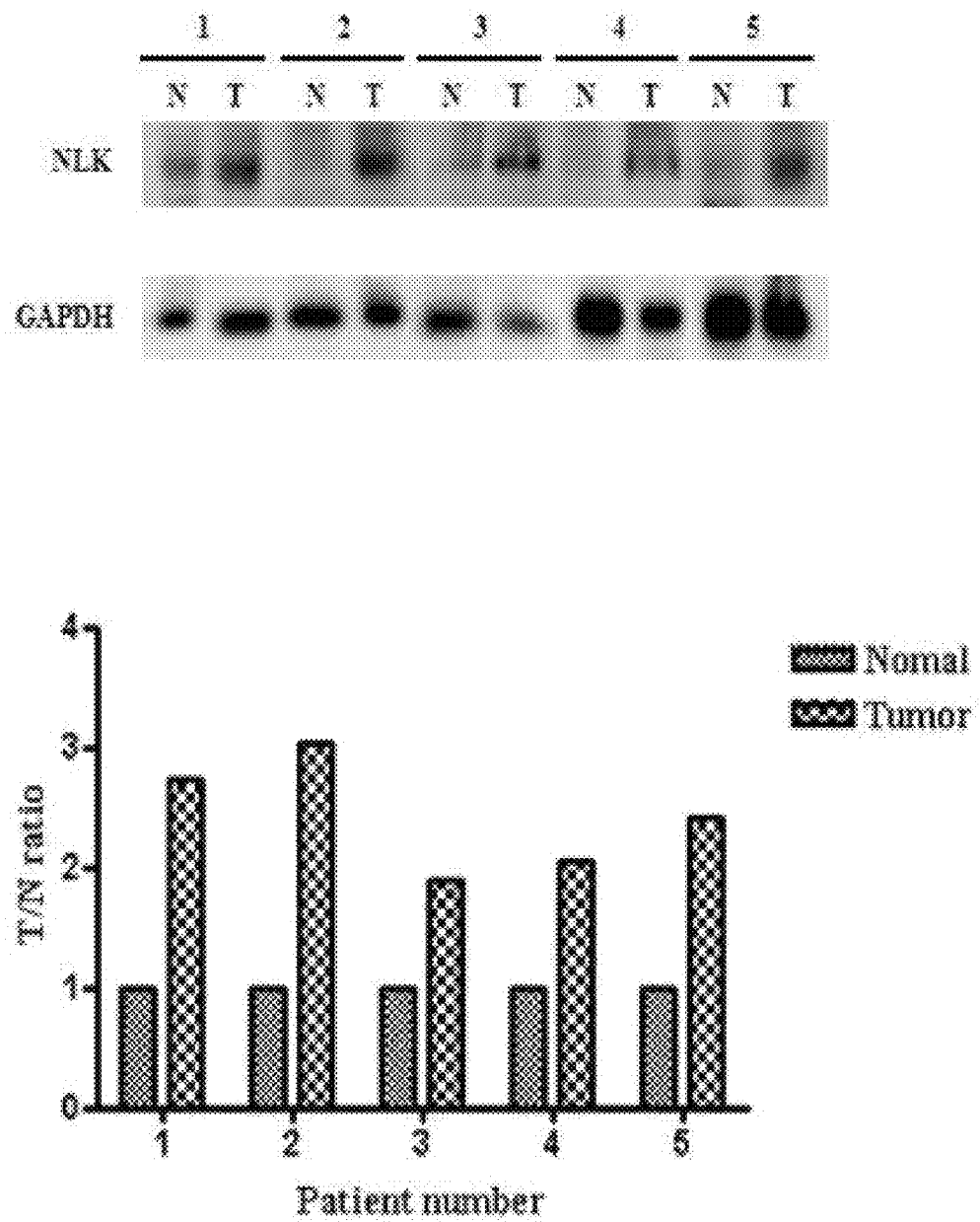
FIG. 2 shows result of analyzing expression level of NLK protein in HCC and normal liver tissue samples by Western blot analysis.
Figure 3:
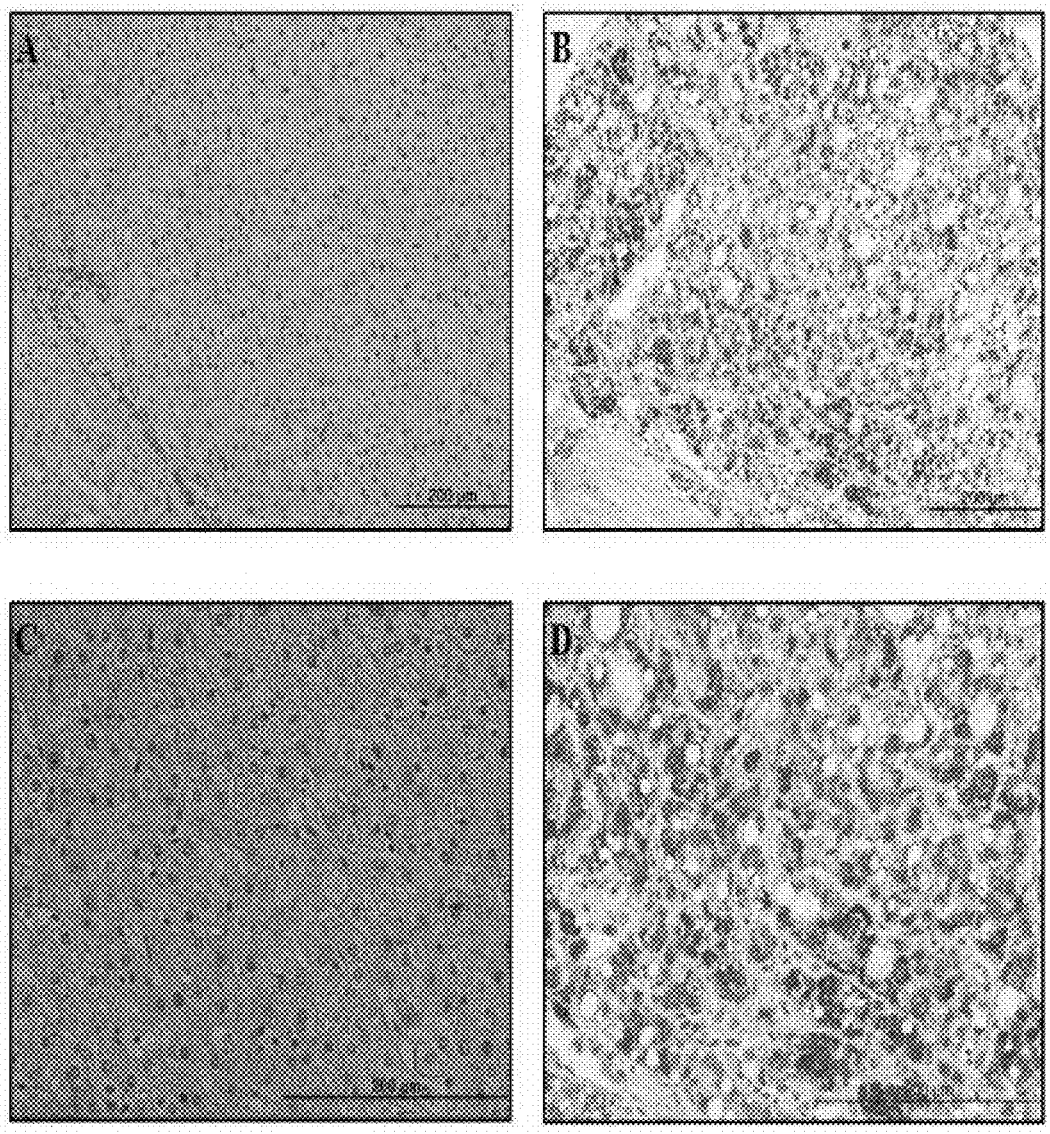
FIG. 3 shows images analyzing normal liver tissues (A and C), and HCC samples (B and D) by immunohistochemical staining on tissue microarray.

As a result of analyzing the expression levels of NLK in HCC and tissues and in normal cells and tissues by RT-PCR and Western blot analysis, in one embodiment, the expression of NLK is up-regulated by at least twofold in HCC tissues compared to the corresponding normal liver tissues (see FIGS. 1 and 2), and the same result was obtained from the immunohistochemical staining (see FIG. 3).

Figure 4:
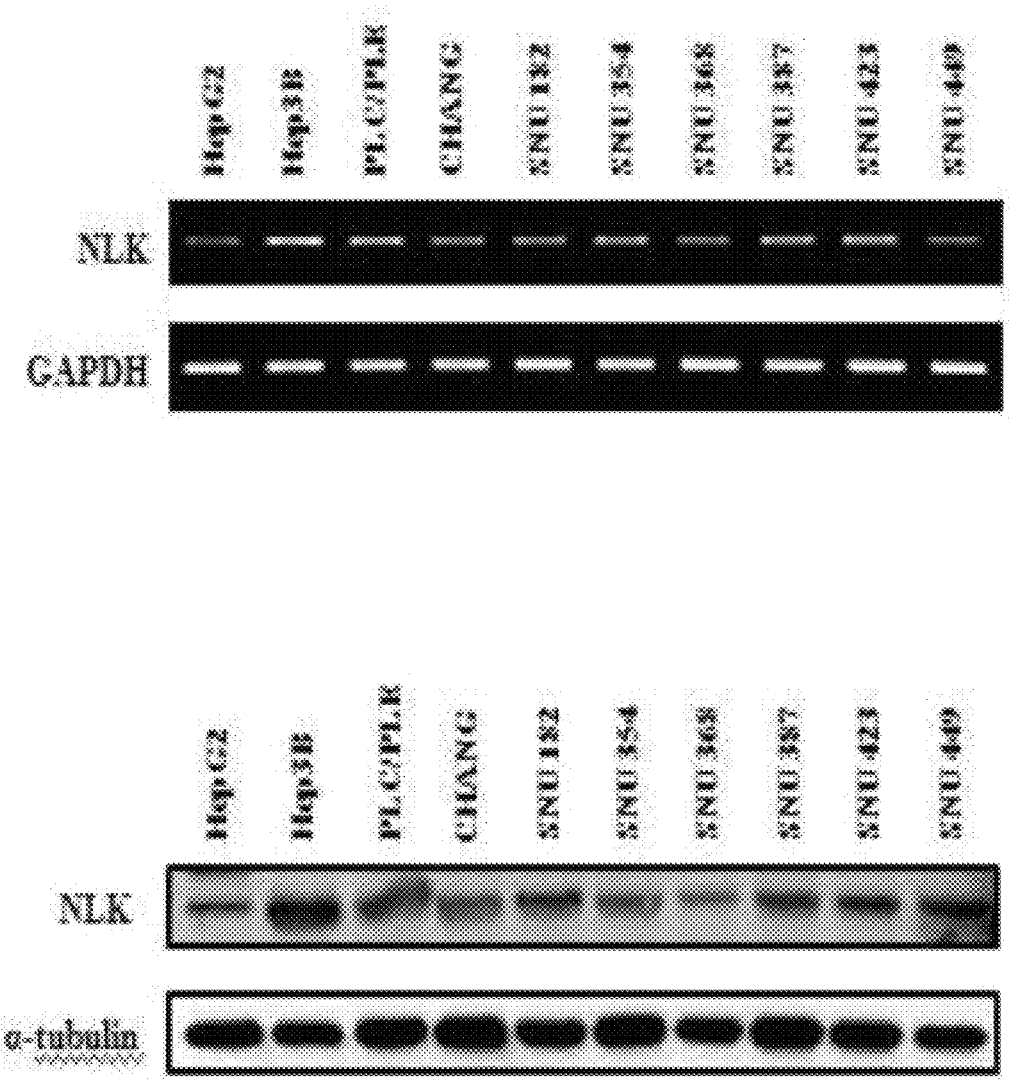
FIG. 4 shows images analyzing expression levels of NLK regarding liver cancer cell lines by RT-PCR (upper image) and Western blot analysis (lower image)

Further, in another embodiment, the over-expression of NLK increased in identical pattern not only in human HCC, but also in other types of liver cancer cells (see FIG. 4).

Considering the above results, the present inventors confirmed that it is possible to diagnose presence of liver cancer based on measurement of expression level of NLK as a marker gene according to the present invention or measurement of level of protein, and were able to provide a composition for diagnosis of liver cancer comprising a substance to measure mRNA or protein level of NLK gene.

Preferably, the expression level of the gene refers to mRNA level, i.e., to an amount of mRNA at which the gene is expressed, and the substance to measure the level may include a primer or a probe specific to the gene. In one embodiment, the primer or the probe specific to the NLK gene may be a primer or a probe that can specifically amplify the entirety of or a specific region of the gene of the NLK, and the primer or the probe may be designed by known method. Preferably, the NLK gene may have a sequence represented by SEQ ID NO: 1, and the primer may be a primer pair of SEQ ID NOs.: 4 and 5 that can amplify the NLK gene.

As used herein, the expression 'primer' refers to single-stranded oligonucleotide that can act as a starting point of template-directed DNA synthesis under proper condition (i.e., four different nucleoside triphosphate and polymerase) at appropriate temperature and appropriate buffer. The appropriate length of the primer may vary depending on various factors such as, for example, temperature and intended use of the primer. Further, the sequence of the primer may not necessarily completely complementary to part of the sequences of the template, because complementarity within a range that can hybridize with the template for primer's unique interaction would be sufficient. Accordingly, in one embodiment, the primer may not necessarily have completely complementary sequence to the sequence of nucleotide of the template gene, but would be sufficient if the primer is hybridized with the gene sequence for primer interaction. Further, the primer according to one embodiment may preferably be used in the gene amplification reaction.

The amplification reaction may refer to a reaction to amplify nucleic acid molecule, and is well known in the art. By way of example, the amplification reaction may include RT-PCR, LCR, TMA, or NASBA.

As used herein, the term "probe" refers to a natural or modified monomer or linear oligomer of linkages, and may include deoxyribonucleotide and ribonucleotide and specifically hybridizable to a target nucleotide sequence, and either naturally occurring or artificially synthesized. In one embodiment, the probe may be single-chain, and preferably, oligodeoxyribonucleotide. The probe in one embodiment may include natural dNMP (i.e., dAMP, dGMP, dCMP and dTMP), nucleotide analogs or derivative. Further, the probe in one embodiment may include ribonucleotide. By way of example, the probe in one embodiment may include backbone-modified nucleotide, for example, peptide nucleic acid (PNA)), phosphorothioate DNA, Dhosphorodithioate DNA, phospnoroamidate DNA, amide-linked DNA, MMI-linked DNA, 2' O-methyl RNA, alpha-DNA and methyphosphonate DNA, glucose modified nucleotide, for example, 2'-O-methyl RNA, 2'-fluoro RNA, 2' amino RNA, 2'-O-alkyl DNA, 2'-O-allyl DNA, 2-O-alkynyl DNA, hexose DNA, pyranosil RNA and anhydrohexitol DNA, and nucleotide with DNA variants, for example, C-5 substituted pyrimidine, (substituents include fluoro-, bromo0, chlroro-, iodo-, methyl-, ethyl-, vinyl-, formyl-, ethytil-, propynyl-, alkynyl-, thizoryl-, imidazoryl-, pyridyl-), 7-deazapurine having C-7 substituent (substituent may include fluoro-, bromo-, chlroro-, iodo-, methyl-, ethyl-, vinyl-, formyl-, alkynyl-, alkenyl-, thizoryl-, imidazoryl-, pyridyl-), inosine and diaminopurine.

The substance to measure the protein level according to one embodiment may include an antibody such as a polyclonal antibody, monoclonal antibody and recombinant antibody which ca specifically bind to protein expressed from NLK marker gene.

As used herein, the term "antibody" may be the one prepared by those skilled in the art using known technology. For example, a polyclonal antibody may be produced by the widely-known method of injecting antigen of the protein into an animal and collecting blood from the animal to obtain serum containing the antibody. The antibody may be prepared from a random animal final host such as goat, rabbit, sheep, monkey, horse, pig, cow, dog, etc. A monoclonal antibody may be produced by a widely-known hybridoma method, or phage display antibody library technology. Further, in one embodiment, the antibodies may be in a complete antibody form, consisting of two full-length light chains and two full-length heavy chains, or may be functional fragments of antibody molecules. The term "functional fragments of antibody molecules" means segments having at least an antigen-binding function, exemplified by Fab, F(ab'), F(ab') 2 and Fv.

Further, the present invention provides a kit for diagnosis of liver cancer, comprising a marker for diagnosis of liver cancer, or a composition for diagnosis of the liver cancer.

The kit for diagnosis of liver cancer according to an embodiment may include a primer, a probe or an antibody to measure expression level of NLK gene as the marker gene, or a level of protein expressed by the gene, each being as defined above.

When applied in the PCR amplification, the kit for diagnosis of liver cancer according to an embodiment may selectively include a reagent necessary for PCR amplification, such as buffer solution, DNA polymerase (e.g., Thermus aquaticus (Taq), Thermus thermophilus (Tth), Thermus filiformis, Thermis flavus, Thermococcus literalis or thermally-stable DNA polymerase obtained from Pyrococcus furiosus (Pfu)), DNA polymerase cofactor, and dNTPs, and when applied in the immuno-analysis, the kit for diagnosis of liver cancer according to an embodiment may selectively include a secondary antibody and a substrate of target. Furthermore, in one embodiment, the kit may be divided into separate packages or compartments containing the respective reagent components explained above, and the kit in one embodiment may be a kit for diagnosis purpose having essential elements necessary to perform DNA chip. The DNA chip kit may include a substrate to which cDNA corresponding to gene or fragment thereof is attached as a probe, and a reagent, agent, enzyme, etc. to prepare fluorescent probe. Further, the substrate may include cDNA corresponding to quantitative control gene or its fragment.

Further, the present invention provides a microarray for diagnosis of liver cancer, comprising the marker for diagnosis of liver cancer or the composition for diagnosis of liver cancer.

In a microarray according to an embodiment, a primer, a probe or an antibody to measure expression level of the marker protein or gene encoding the same may be used as a hybridizable array element, and fixed on the substrate. The substrate may preferably be proper rigid or semi-rigid support, such as, for example, membrane, filter, chip, slide, wafer, fiber, magnetic bead or non-magnetic bead, gel, tubing, plate, polymer, microparticle, or capillary tube. The hybridized array element may be arranged on and fixed in the substrate, in which the fixation may be performed by chemical bonding or covalent bonding such as UV. By way of example, the hybridized array element may be bound to glass surface which is modified to include epoxy compound or aldehyde group, or alternatively, the hybridized array element may be bound onto polylysine-coating surface by UV. Further, the hybridized array element may be bound to the substrate via a linker (e.g., ethylene glycol oligomer and diamine).

Meanwhile, the nucleic acid as the reagent applied to the microarray may be labeled, and hybridized with an array element on the microarray. The condition for hybridization may be variously implemented, in which detection and analysis of the degree of hybridization may also be variously implemented depending on marker substance.

Further, the present invention may provide a method for predicting and diagnosing liver cancer by using a method for measuring expression level of NLK marker gene or expression protein level thereof, which includes: (a) measuring expression level of NLK gene or level of protein encoded by the gene from a biological sample of a patient with suspected liver cancer; and (b) comparing the expression level of the gene or the level of the protein encoded by the gene with expression level of a gene corresponding to a normal control or protein level thereof.

The method for measuring the expression level of the gene or the level of protein may include known processing to separate mRNA or protein from a biological sample.

In one embodiment, the expression "biological sample" may refer to a sample taken from a living organism different from a normal control with normal expression level of the gene or protein level according to development or progression of the liver cancer, in which the sample may include tissue, cell, blood, serum, plasma, saline, and urine.

The expression level of the gene may be measured by measuring mRNA level, in which the level of mRNA may be measured by RT-PCR, RNase protective analysis, Northern blot analysis, and DNA chip, but not limited thereto.

An antibody may be used to measure the protein level, in which case the marker protein within the biological sample and the antibody specific thereto may associate to form antigen-antibody complex, and the amount of formation of antigen-antibody complex may be quantitatively measured based on the size of signal of the detection label. The detection label may be selected from a group consisting of enzyme, fluorescence, ligand, illuminator, microparticle, redox molecule and radioactive isotope, but not limited thereto. The analysis method for measuring protein level may include Western blot analysis, ELISA, radioimmunoassay, radioimmunodiffusion, ouchterlony immunodiffusion, rocket immunoelectrophoresis, tissue immunohistochemistry, immunoprecipitation assay, complement fixation assay, FACS, and protein chips, but not limited thereto.

Accordingly, through the detection methods explained above, the present invention can measure the expression level of mRNA of a marker gene or protein amount of a control and measure the expression level of mRNA of a marker gene or protein amount from a patient with confirmed or suspected liver cancer, and predict or diagnose onset of the liver cancer, developing stage thereof, or prognosis of the liver cancer based on the comparison of the expression levels with the control.

To be specific, the method for predicting or diagnosing onset of liver cancer may determine that the liver cancer has occurred when the expression level of NLK gene, which is a marker gene for liver cancer according to an embodiment, or amount of expressed protein is up-regulated compared to the normal control sample.

Furthermore, the present invention may provide a method for screening a substance for preventing or treating liver cancer, comprising steps of: (a) contacting a marker gene according to an embodiment for diagnosis of liver cancer or expressed protein thereof with a liver cancer cell or tissue; (b) measuring expression level of the selected gene or amount of expressed protein thereof; and (c) as a result of measurement at (b), if the expression level of the selected gene or the amount or activity of expressed protein is down-regulated, determining the sample to be a substance for preventing or treating the liver cancer.

In one embodiment, the screening method may contact a sample of interest to the liver cancer cell containing the gene or protein. The sample refers to an unknown substance used in the screening to investigate whether or not the sample influences the expression level of the gene, amount of the protein, or activity of the protein. The sample may include a chemical substance, oligonucleotide, antisense-RNA, siRNA (small interference RNA), shRNA or natural extract, but not limited thereto. The expression level of the gene, level of protein or activity of protein may be measured from the cell treated with the sample, and if up-regulation or down-regulation of the expression level of the gene, level of protein or activity of protein is detected as a result of detection, the substance may be determined to be the substance to treat or prevent the liver cancer.

The expression level of the gene, level of protein or activity of protein may be measured by various known methods in the pertinent art. By way of example, reverse transcriptase-polymerase chain reaction, real time-polymerase chain reaction, Western blot analysis, Northern blot analysis, ELISA (enzyme linked immunosorbent assay), radioimmunoassay (RIA), radioimmunodiffusion and immunoprecipitation assay may be used for the measurement, but not limited thereto.

Meanwhile, in addition to the fact that NLL is over-expressed in the liver cancer tissue than in normal tissue, the present inventors can also discover the relationship between NLK and expression of cyclin D1 and CDK2, the cell cycle regulators. That is, the present inventors were the first to discover that the expression of NLK inhibits expression of cyclin D1 and CDK2, the cell cycle regulators.

Accordingly, by inhibiting the expression of NLK gene, the present invention provides a method for simultaneously inhibiting the expression of cyclin D1 and CDK2, and regulating cell cycle of mitosis. Further, the present invention provides a composition for preventing or treating liver cancer, comprising a substance to simultaneously inhibit the expression of both cyclin D1 and CDK2.

Generally, cell cycle progresses in a predetermined order according to a mechanism set in the cells. If the predetermined order is disrupted, the cell cycle can hardly be maintained, and cyclin and Cdk are the regulators that play the role of recovering the original cell cycle when disruption occurs. In the cell cycle, it is reported that Cdk4, 6, 8 are activated depending on the type of cells in the beginning phase of G1, Cdk2 operates in the late phase of G1 and beginning phase of S, and Cdk1 (Cdc2) plays an important role in the transition from G2 to M.

Association with cyclin is essential for the activation of Cdk, in which Cdk4, 6, 8 are activated by associating with cyclin D, while Cdk2 is associated with cyclin A and E. Cdk1 is associated with cyclin B and A. Other than the above, cyclin G, F, etc., are also known. Since cyclin-Cdk complex specific to the respective phases of the cell cycle is respectively activated, and proteins phosphorylated specifically to Cdk are responsible for the progression of cell cycle, the cell cycle is sometimes called Cdk cycle.

Further, Cdk is an essential factor for the activation of cyclin. The activated Cdk-cyclin is divided into cyclin regulating unit and Cdk activation unit, and the method for regulating cyclin Cdk may be two-fold: that is, one is that cycline and Cdk are associated to induce structural change in the protein so that the ATP phosphate group is arranged to be easily transferred to the substrate protein. Further, the location of T loop, which blocks the access of the substrate of the protein from Cdk, changes to permit access of the substrate. Cdk is activated at a particular period because of cyclin synthesis which takes place specifically to cell cycle.

Further, cyclin D synthesis is at the peak mainly in the intermediate phase of G1, and is induced by mitogen of cell growth factors, etc. Cyclin D is mainly divided into three sub-types (D1, D2, D3) which have different expression levels depending on types of the cells. For example, cell cycle G1 is arrested if cyclin D synthesis is inhibited, and if cyclin D is over-expressed, G1 is shortened and the cell cycle begins without mitogen.

Meanwhile, the present inventors observed the variations in the expression of cyclin D1 and CDK2 and activities of the related transcriptional factors, when the expression of NLK is inhibited using siRNA regarding NLK, the marker gene for diagnosis of liver cancer according to an embodiment. To be specific, the inhibition of NLK by NLK siRNA accompanies with simultaneous expression inhibition of cyclin D1 and CDK2 (see FIGS. 8 and 10).

Further, in one embodiment, in terms of the phosphorylation of p130 and retinoblastoma protein (pRb), which indicate direct relationship between NLK and CDK2 and cyclin D1 expression, it was observed that inhibited expression of NLK is led into decreased phosphorylation of p130, and via transcriptional activity of CDK2 and cyclin D1, this also influenced phosphorylation of the pRb protein family. In other words, the inhibition of gene expression of NLK has inhibited phosphorylation of pRB and p130 proteins, which in turn caused decreased transcriptional activity of CDK2 and cyclin D1 (see FIG. 10).

Figure 11:
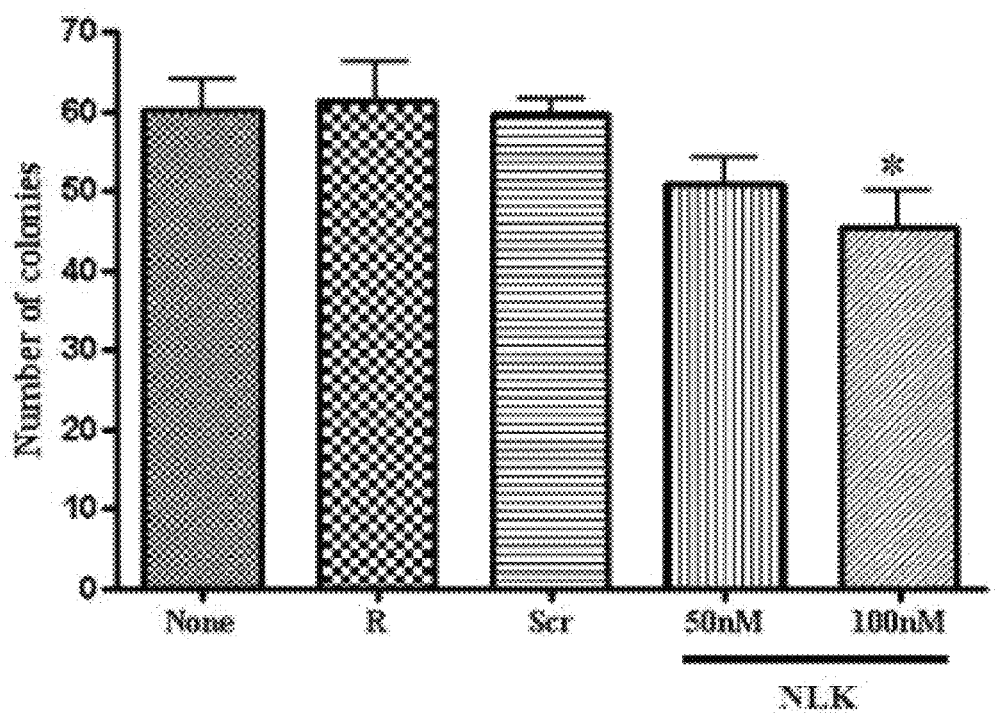
FIG. 11 shows graphs comparing the results of inhibiting NLK expression in cells using NLK siRNA, i.e., comparing colony formation in HCC between controls (Scr: treated with scrambled siRNA, R: treated only with reagent, and None: treated with none.

Further, in one embodiment, when the NLK expression was inhibited in the liver cancer cell, proliferation of the liver cancer cell was inhibited, and to be specific, the anchorage-independent growth was decreased (see FIG. 11). On the contrary, it was confirmed that the inhibition of NLK expression did not give any influence on the apoptosis of liver cancer cell (see FIG. 9).

Based on the above results, the present inventors were able to confirm the fact that, when the expression of NLK is inhibited in the liver cancer cell, the expression of cyclin D1 and CDK2, the cell cycle regulators, were down-regulated so that progression of cell cycle is arrested, and in the end, anticancer activity is provided by the inhibition of proliferation of liver cancer cells.

Therefore, the present invention provides a composition for preventing or treating liver cancer, comprising oligonucleotide to inhibit expression of NLK as an effective component.

Preferably, the oligonucleotide to inhibit expression of the NLK may be antisense oligonucleotide, RNAi, siRNA or shRNA regarding a NLK gene expressed by SEQ ID NO: 1, and the siRNA may have a sequence of SEQ ID NO: 2 or SEQ ID NO: 3.

According to an embodiment, the term "antisense oligonucleotide" refers to DNA or RNA containing nucleic acid sequence complementary to a specific mRNA sequence, or derivative thereof, and this binds to the complementary sequence within mRNA to impede mRNA translation into protein. In one embodiment, the antisense sequence refers to DNA or RNA sequence which is complementary to mRNA of said gene and which can bind to the mRNA, and this can impede essential activity regarding the mRNA's translation, translocation into cytoplasm, maturation, or all the other entire biological functions.

Further, the antisense nucleic acid may be modified at a site of at least one base, glucose or backbone to enhance efficacy. The backbone of nucleic acid may be modified by phosphorothioates, phosphotriesters, methyl phosphonates, short chain alkyl or cycloalkyl or short chain heteroatomic or heterocyclic intersugar linkages. Further, the antisense nucleic acid may include at least one substituted sugar moiety. The antisense nucleic acid may include modified base. The modified base may include hypoxanthine, 6-methyladenine, 5-Me pyrimidines (particularly 5-methylcytosine), 5-hydroxymethylcytosine (HMC), glycosyl HMC and gentobiosyl HMC, as well as 2-aminoadenine, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. Further, the antisense nucleic acid in one embodiment may be chemically linked to one or more moieties or conjugates that enhance the activity, or cellular uptake of the antisense nucleic acid. Such moieties comprise but are not limited to, lipid moieties such as a cholesterol moiety, cholic acid, a thioether, a thiocholesterol, an aliphatic chain, a phospholipid, a polyamine or a polyethylene glycol chain, or adamantane acetic acid, a palmityl moiety, or an octadecylamine or hexylamino-carbonyl-oxycholesterol moiety. The oligonucleotide containing lipid moieties and a preparation method thereof are well known in the pertinent field. The modified nucleic acid may increase stability to nuclease and also enhance binding affinity between antisense nucleic acid and target mRNA.

The antisense oligonucleotide may be synthesized in vitro in a conventional manner and administered into a living body, or the antisense oligonucleotide may be synthesized in vivo. One example of synthesizing antisense oligonucleotide in vitro uses RNA polymerase I. One example of synthesizing antisense RNA in vivo uses a vector with MCS origin in opposite direction to induce antisense RNA transcription. It is preferable that translation termination codon is present within the sequence to prevent translation of such antisense RNA into peptide sequence.

As used herein, the expression "RNAi" refers to RNA interference. The RNA interference is specific genetic inhibition phenomenon that is well preserved among most living organisms. This is considered to be one of genetic surveillance mechanisms used by the cells to defend against virus inflammation, to inhibit transposon, or to eliminate abnormal mRNA. To be specific, in a broad sense, the gene silencing phenomenon by small RNA is the RNA interference, and the mRNA decomposition by siRNA is the RNA interference in a narrow sense. Further, the RNA interference also refers to gene silencing test technology using siRNA.

As used herein, the expression "siRNA" refers to a nucleic acid molecule that can mediate RNA interference or gene silencing. Since siRNA can suppress target gene, this is provided as an efficient knock-down method or gene therapy.

In one embodiment, a siRNA molecule may have a double-chain structure in which the sense strand (sequence corresponding to mRNA sequence of the marker gene) and the antisense strand (sequence complementary to the mRNA sequence) are located opposite to each other. Further, the siRNA molecule in one embodiment may have a single-chain structure of the self-complementary sense and antisense strands. Furthermore, it is not strictly limited that siRNA has the double-chain RNA parts in complete pair with RNA. Accordingly, the siRNA is not limited to the form of complete base pairs in the double RNA strands, but may be in partially unpaired forms resulting from mismatch (corresponding bases are not complementary) or bulginess (lack of corresponding bases in one strand). Further, the siRNA end may be blunt or cohesive end as long as the expression of the marker gene is inhibited by the RNAi effect, in which the cohesive end structure may include both 3'-overhang end and 5'-overhang end.

Further, the siRNA molecule in one embodiment may have a form in which a short nucloetide sequence is inserted between the self-complementary sense and antisense strands, in which case the siRNA molecule formed by the expression of the nucleotide sequence forms hairpin structure by the intermolecular hybridization, and forms stem-and-loop structure as a whole. The stem-and-loop structure generates active siRNA molecule which is processed in vitro or in vivo to mediate RNAi.

The method for producing siRNA may include a method for directly synthesizing siRNA in vitro and then introducing into cell by transfection, and a method for transfecting or infecting siRNA expression vector or PCR-derived siRNA expression cassette which is so designed to express siRNA within cells.

Further, a composition containing a gene specific siRNA according to an embodiment may include an agent for promoting the introduction of siRNA into a cell. This agent may be a promoter for the introduction of nucleic acids. For example, liposomes may be used alone or in combination with one type of lipophilic carrier selected from among sterols including cholesterol, cholate and deoxycholic acid. For the intracellular introduction of siRNA, cationic polymers, such as poly-L-lysine, spermine, polysilazane, PEI (polyethylenimine), polydihydroimidazolenium, polyallylamine, chitosan, etc. or anionic polymers, such as succinylated PLL, succinylated PEI, polyglutamic acid, polyaspartic acid, polyacrylic acid, polymethacrylic acid, dextran sulfate, heparin, hyaluronic acid, etc., may be used.

When an antibody specific to the protein is used as a substance to up-regulate or down-regulate the expression of activity of the marker protein, the antibody can be coupled (e.g., covalently bonded) with a preexisting drug directly or indirectly, that is, via a liker. Examples of the drug coupled with antibodies include radionuclides, pharmaceuticals, lymphokine, toxins, and heterofunctional antibodies, but are not limited thereto. (1) Radionucleotides, such as $^{131}$I, $^{90}$Y, $^{105}$Rh, $^{47}$Sc, $^{67}$Cu, $^{212}$Bi, $^{211}$At, $^{67}$Ga, $^{125}$I, $^{186}$Re, $^{188}$Re, $^{177}$Lu, $^{153}$Sm, $^{123}$I, and $^{111}$In, (2) biological reaction modifiers or biological reaction-modifying drugs, such as methotrexate, adriamycin, and lymphokines including interferons, (3) toxins, such as ricin, abrin, and diphtheria, (4) heterofunctional antibodies, that is, complexes formed by conjugating heterotype antibodies with each other, which are able to bind both to cancer cells and to effector cells (e.g., killer cells such as T cells), and (5) natural, that is, non-related or non-complexed antibodies may be coupled with the antibody according to the present invention.

Further, the composition for preventing or treating liver cancer according to an embodiment is a pharmaceutical composition to treat liver cancer, and may additionally include a pharmaceutically-acceptable carrier. The expression "pharmaceutically-acceptable" refers to a composition that is biologically acceptable and does not generally cause allergic reaction such as gastroenteric touble or dizziness, or similar reaction, when administered to a human. An example of the pharmaceutically-acceptable carrier includes, for example, orally-administered carrier such as lactose, starch, cellulose derivative, magnesium stearate, or stearic acid, and parenterally-administered carrier such as water, proper oil, saline solution, aqueous glucose and glycol, and may additionally include stabilizer and preservative. The proper stabilizer may include antioxidant such as sodium bisulfite, sodium sulfite, or ascorbic acid. The proper preservative may include benzalkonium chloride, methyl- or propyl-parabene and chlorobutanol. For other pharmaceutically-acceptable carriers, reference is made to the Remington's Pharmaceutical Sciences, 19th ed., Mack Publishing Company, Easton, Pa., 1995. The pharmaceutical composition in one embodiment and the pharmaceutically-acceptable carrier may be formulated into suitable form according to known methods. That is, the pharmaceutical composition in one embodiment may be formulated into various preparations for oral or parental administration. A representative example of the preparation for parental administration is isotonic aqueous solution or suspension for injection. The preparation for injection may be prepared by the known methods using proper dispersant or wetting agent or suspending agent. By way of example, the respective ingredients may be dissolved in saline solution or buffer solution to be prepared for injection. Further, the preparation for oral administration may include, but not limited thereto, powder, granule, pill, tablet and capsule.

The pharmaceutical composition formulated in the manner explained above may be administered in effective amount by various routes including oral, percutaneous, subcutaneous, intravenous, or intramuscular routes, in which the 'administration' refers to introducing a predetermined substance to a patient by a certain proper method, and the route of administering the substance may be a certain general route that can lead to a target tissue.

Further, the 'effective amount' refers to an amount that is administered to a patient and shows preventive or treatment efficacy. The amount of administration of the pharmaceutical composition in one embodiment may vary depending on various factors including type and severity of a patient's disease, age, sex, body weight, sensitivity to drug, currently-prescribed therapy, method of administration, or target cell, which may be easily determined by those skilled in the art. Further, the pharmaceutical composition according to an embodiment may be administered in combination with conventional drug, either sequentially or simultaneously, and also by single administration or multi-administration. A preferable amount may be a minimum amount that can obtain maximum effect in consideration of all the above-mentioned factors, without causing any side effect. More preferably, the effective amount may range between 1~10000 μg/(weight) kg/day, or even more preferably, between 10~1000 mg/(weight) kg/day and may be administered several times a day.

The present invention will be explained in greater detail below with reference to Examples. However, these examples are written only for illustrative purpose, and one skilled in the art will be able to understand that the scope of the present invention is not limited by these examples only.

EXAMPLE 1

Preparation of Microarray (1) Tissue microarray (TMA)

Five frozen HCCs and their corresponding normal background liver tissue samples from five patients with HCC (all Korean Patients) were evaluated in this study. The background liver showed chronic hepatitis in all cases and HBV was detected in all cases. Approval was obtained from the institutional review board of the Catholic University of Korea (CUMC09U029), College of Medicine. Informed consent was provided by every patient according to the Declaration of Helsinki. Frozen tissues were ground to a very fine powder in liquid nitrogen, and then were preserved for molecular testing. For tissue microarray (TMA) construction, a total of 50 liver samples (30 HCCs and 20 normal liver tissues) of formalin fixed, paraffin-embedded liver samples were obtained from the archives of the Department of Pathology at the Catholic University of Korea, College of Medicine. Two replicate core samples of neoplastic tissue and normal liver tissue were punched out of each donor-tumor block and placed into recipient paraffin blocks using a 0.6 mm diameter stylet.

(2) Cell Culture

Human liver cancer cell line HepG2, Hep3B, PLC/PRF/5, CHANG, SNU-182, SNU-387, SNU-423 and SNU-449 were purchased from the American Type Culture Collection (ATCC; Manassas, Va.). Then, human liver cancer cell line SNU-354 and SNU-368 were purchased from Korean Cell Line Bank (KCLB, Korea). The cells were maintained in RPMI 1640 or DMEM medium supplemented with 10% fetal bovine serum (Sigma, St Louis, Mo.) and 1 mg/ml of penicillin/streptomycin (Invitrogen, Grand Island, N.Y.).

EXAMPLE 2

Measurement of mRNA and Protein Expression of NLK

The present inventors investigated mRNA expression of NLK (neuro-like kinase) by conducting RT-PCR with respect to the above-mentioned five HCC tissue and normal liver tissue samples selected from the patients. To this purpose, the inventors first extracted total RNA using TRIzol (Invitrogen, Carlsbad, Calif., USA) and performed quality control using RNA 6000 Nanochips on an Agilent 2001 Bio analyzer (Agilent Technologies, Germany). Then, 1 μg RNA was used for cDNA synthesis reaction using RNA PCR Core Kit (Roche, Branchburg, N.J., USA). cDNA was used per reverse transcription-PCR(RT-PCR) reaction. RT-PCR program was 95° C. 30 s, 53° C. 30 s, and 72° C. 30 s for 35 cycles. RT-PCR primer sequences are as follows:

RT-PCR primer sequences

```
NLK forward (SEQ ID NO: 4):
5'-GCT GGA TAT TGA GCC GGA TA-3'

NLK reverse (SEQ ID NO: 5):
5'-CAT CTT CAA TTC CCG GAA GA-3'

GAPDH forward (SEQ ID NO: 6):
5'-ACC AGG TGG TCT CCT CTG AC-3'

GAPDH reverse (SEQ ID NO: 7):
5'-TGC TGT AGC CAA ATT CGT TG-3'
```

In addition to the RT-PCR, the present inventors also measured the expression level of NLK in the liver cancer tissues by Western blot analysis. For this measurement, whole-cell extracts were prepared with radio-immunoprecipitation assay (RIPA) lysis buffer (50 mmol/L Tris-HCl, pH7.4, 150 mmol/L NaCl, 1% Nonidet P-40, 0.25% sodium deoxycholate, 1 mmol/L Phenylmethane-sulfonylfluoride containing protease inhibitors, Roche, Mannheim, Germany). Protein concentrations were determined using the BCA protein assay kit (Pierce, Rockford, Ill.) and absorbance of the protein samples were read at 570 nm with the VICTOR3™ Multilabel Plate Reader (PerkinElmer). RIPA lysates containing 10 μg or 15 μg of protein were separated by SDS-PAGE and transferred onto a polyvinylidene difluoride membrane (Amersham Hybond™-P, Little Chalfont, Buckinghamshire, UK) and kept in 5% skim milk (BD Biosciences) in TBS solution containing 0.05% Tween-20 (Usb Corporation, Cleveland, Ohio) overnight to protect against non-specific binding. The membranes were incubated with each of the primary antibodies and horseradish peroxidase (HRP)-conjugated secondary antibodies (Pierce). The ECL plus Western blotting detection system (Amersham) was used to detect immobilized specific antigens conjugated to HRP labeled antibodies. The membrane was exposed to LAS 3000 (Fuji Photo Film Co. LTD, Japan) to measure the amount of expressed protein.

As shown in FIG. 1a, the mRNA expression of NLK was up-regulated by at least twofold in the HCC samples compared to the corresponding normal liver tissues. Similarly, when NLK protein expression was assessed by Western blot analysis, expression of NLK was markedly up-regulated in all tested HCCs.

Based on the above results, the present inventors were able to confirm that the NLK is associated with the initiation of the liver cancer, and more specifically, could confirm that NLK can be used as a marker for diagnosis of liver cancer.

EXAMPLE 3

Immunohistochemistry Analysis of NLK

As a result of Example 2 explained above, it was confirmed that NLK is over-expressed in liver cancer tissue, and this was further investigated by immunohistochemistry analysis.

(1) Immunohistochemical Staining

To investigate the level of NLK protein in HCC, the inventors performed immunohistochemical staining with monoclonal antibodies against NLK (1:50, Abcam, Cambridge, UK) on TMA samples of HCC. Prior to the immunostaining, the TMA slides were deparaffinized and hydrated through graded ethanol to deionize the water. Endogenous peroxidase activity activity was blocked by 5 min incubation in 3% hydrogen peroxide-methanol buffer. Antigens were retrieved by boiling the slides in a streamer with sodium citrate buffer (pH 6.0) for 20 min. After incubation with monoclonal antibodies against NLK overnight at 4° C., detection was carried out using biotinylated goat anti-mouse antibodies (1:200; Sigma), followed by incubation with the peroxidase-linked avidin-biotin complex. Diaminobenzidine was used as the chromogen, and the slides were then lightly counterstained with Mayer's hematoxylin. As a negative control, the slides were treated and the primary antibody was replaced by non-immune serum.

As a result, as shown in FIGS. 3c and 3d, NLK localized to the cytoplasm and nucleus in all of the HCC cases.

(2) Evaluation of Immunohistochemical Staining

Scoring of the TMA was performed independently by two pathologists. In the event of disagreement, the two reached a consensus by jointly re-evaluating the TMA using a multihead microscope. Immunostaining intensity was graded in three categories: 1+(weak), 2+(moderate), and 3+(strong). However, if the number of immunostained cells was less than 10%, the case was considered to be negative for staining. Each two replicate core tumor tissues were combined and calculated as one case.

As a result, among the 20 samples tested of normal hepatocytes, 16 (80%) had weak positive or no detectable to NLK antibody, while 17 (54%) out of 30 tested HCCs showed moderate or strong positive to NLK antibody staining.

(3) Comparison of Various Hepatoma Cell Lines

The inventors also examined NLK expression levels of human hepatoma cell lines in tissues other than HCC tissues. That is, the inventors took 10 different human hepatoma cell lines which were originally established from HCCs or hepatoblastomas, and determined expression of NLK by RT-PCR and Western blot analysis.

As shown in FIG. 4, NLK was over-expressed than normal counterpart, and among the hepatoma cell lines, Hep3B cells were appeared to be highest expression level of NLK.

EXAMPLE 4

HCC Proliferation Assay by NLK Interference (1) NLK Expression Silencing

To explain the consequences of inhibiting gene expression of NLK, NLK was endogenously disrupted by the RNA interference-mediated protein knock-down method in Hep3B cells. To this purpose, the NLK siRNA and scrambled siRNA were purchased from Ambion Inc (Ambion, Austin, Tex.).

The targeted NLK sequences were 5'-GGGUCUUCCGG-GAAUUGAA(tt)-3' (sense) [SEQ ID NO:2] and 5'-UUCAA-UUCCCGGAAGACCC(tt)-3' (antisense) [SEQ ID NO:3]. The cells were harvested by Trypsin/EDTA, replated at $1.5 \times 10^5$ cells in a 60 mm dish, and allowed to grow overnight at 37° C. in a humidified incubator at 5% $CO_2$. After 16 h of plating, the cells were transfected with none, reagent only, 50 nmol/L scrambled siRNA, 50 nmol/L or 100 nmol/L NLK-specific siRNA in Opti-MEM (Invitrogen). Transfection was carried out using 10 μl of lipofectamine 2000 reagent (Invitrogen) according to the manufacturer's specifications. After 6 h of transfection, the medium was replaced by new fresh RPMI 1640 medium supplemented with 10% FBS. After that, NLK silencing was performed using NLK-specific siRNAs, and level of NLK expression inhibition by the NLK-targeting siRNA was evaluated by RP-PCR and Western blot analysis.

Figure 5:
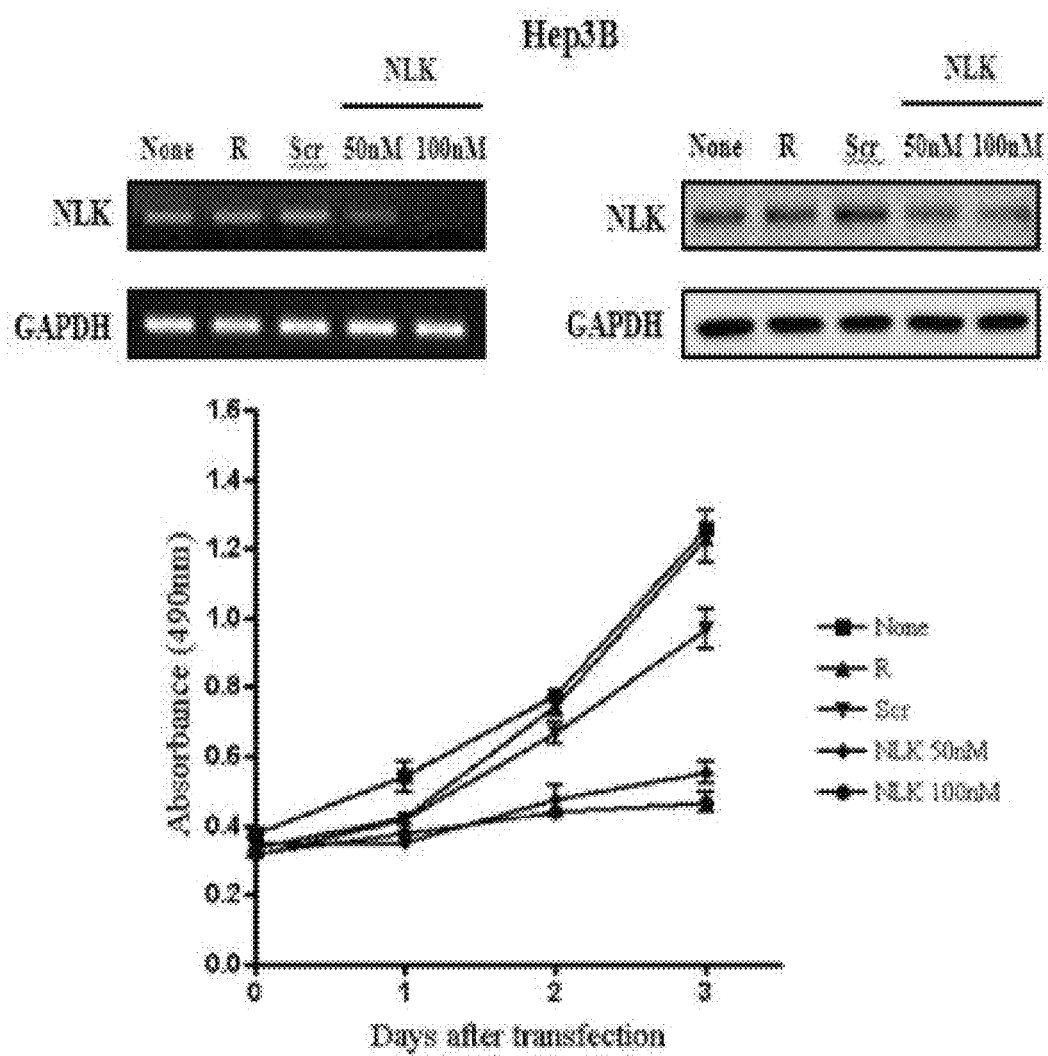
FIG. 5 shows images analyzing after silencing NLK in Hep3B cell using NLK siRNA by RT-PCR and Western blot analysis, and graph shows growth rate of the cells by MTS analysis.

As a result, as shown in FIG. 5, compared to the control (introduced with scrambled sequence), the two cases of treating cells with 50 nM and 100 nM of NLK siRNA showed effectively inhibited NLK expression in Hep3B cells.

(2) Cell Proliferation Assay

The influence on the growth of Hep3B cells when NLK expression is inhibited by NLK siRNA was investigated with MTS assay. To this purpose, the cells were plated in a 24-well culture plate at a density of $2 \times 10^4$ cells per well with RPMI 1640 medium with 10% FBS and maintained for 18 h. Four hours after the NLK specific siRNA transfection, RPMI 1640 medium with 10% FBS was replaced in each of the 24-wells in the culture plate and the cells were maintained at 37° C. in a 5% $CO_2$ humidified incubator. To determine cell proliferation, the cells were incubated with 200 μl of the CellTiter 96® AQueous One Solution Cell proliferation Assay solution (Promega, Madison, Wis.) at each indicated time (0, 1, 2 and 3 days). Three hours after incubation, absorbance of the cells was determined with a VICTOR3™ Multilabel plate reader (PerkinElmer Inc, Boston, Mass.). Further, to verify the fact that NLK promotes hepatic tumor growth, the inventors took another cell lines, disrupted NLK expression and analyzed the growth rate of the cells.

As a result, as shown in FIG. 5, silencing of NLK significantly decreased the cell growth rate at both the 50 and 100 nM of NLK siRNA concentrations compared to cells treated with the scrambled siRNA.

Figure 6:
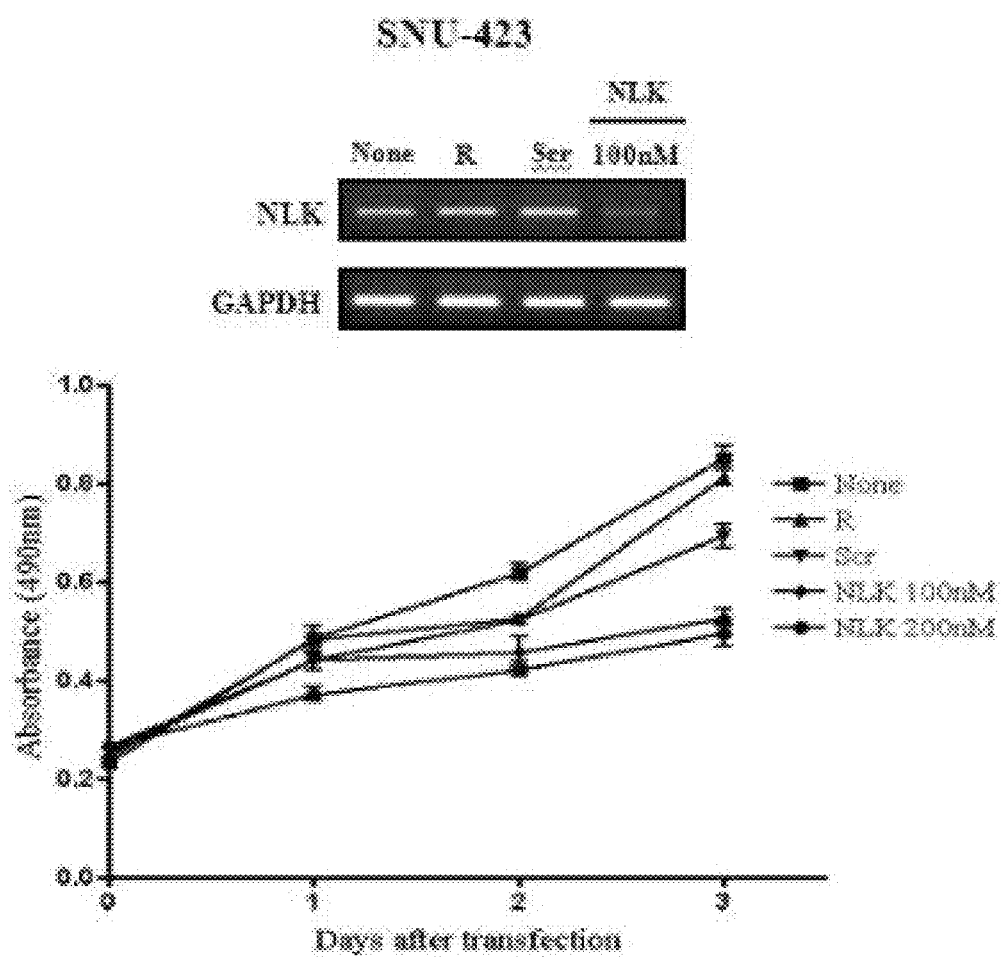
FIGS. 6 and 7 show images comparing expression levels of NLK and growth rates between scrambled siRNA and controls treated with reagent only, after treating NLK siRNA to SNU-423 and SNU-368 cell lines.
Figure 7:
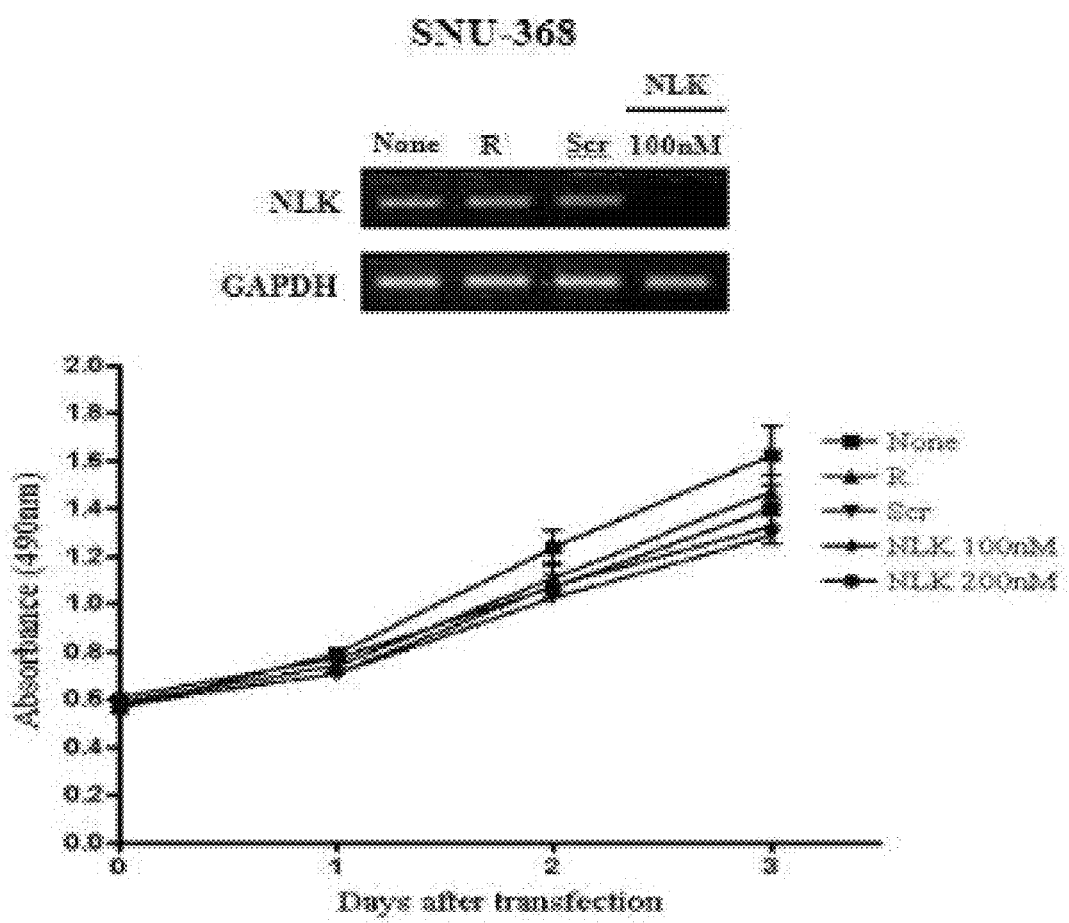

As shown in FIGS. 6 and 7, when the expression of NLK was suppressed in other tumor cell lines, SNU-423 cells' growth rate was reduced. However, SNU-368 cells did not display the reduced growth rate.

Accordingly, the above result indicates that aberrant regulation of NLK stimulates cell growth specifically in human HCCs, and this accordingly suggests the fact that NLK can be used as a marker specific to liver cancer.

EXAMPLE 5

Cell Cycle Analysis of HCC Cells with Inhibited Expression

From the above-explained result, the present inventors could confirm the fact that NLK is over-expressed in the liver cancer cell, and to investigate if inhibiting NLK expression can provide effect of preventing or treating liver cancer, investigated changes of cell cycles based on the Hep3 cells with RNA of NLK silenced. To this purpose, 48 h after transfection with NLK siRNA, the cells were harvested, washed with cold PBS and fixed in 70% alcohol for 1 day at −20° C. After fixation, the cells were washed again with cold PBS twice and incubated for 30 min in PBS containing 10 mg/ml of RNase A at 37° C. After RNase A treatment, the nuclei were stained with 5 mg/ml of propidium iodide (PI), and stained cells were measured by fluorescence-activated cell sorting (FACS) on a FACScan apparatus. The data obtained was analyzed by Cell-Quest FACS analysis software (BD Biosciences, Franklin Lakes, N.J.). To measure the change of cell cycle transition by NLK siRNA transfection, gated single cell population from all cell population in the FL2-A/FL2-W plot was analyzed according to Cell-Quest FACS analysis software protocol.

Figure 8:
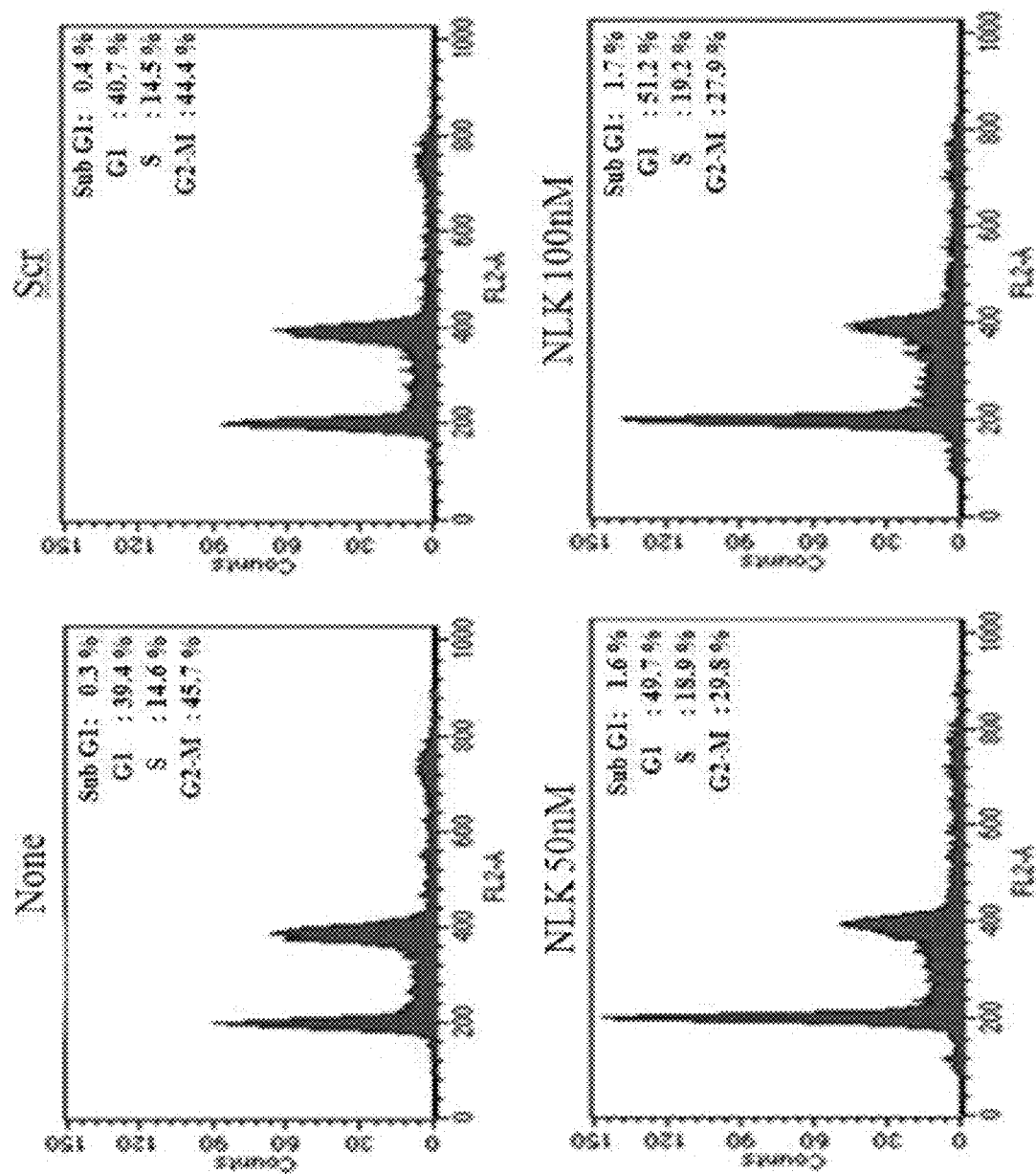
FIG. 8 shows images analyzing cell cycle by PI staining, after inhibiting NLK expression in Hep3B cell using NLK siRNA.

As a result, as shown in FIG. 8, when the Hep 3B cells were analyzed by flow cytometry, 48 h after transfection with or without NLK siRNA, the PI stained cells showed that the cell population during the G1-S phase was increased by NLK siRNA transfection. It appeared that the NLK knock-down augmented G1 cycle arrest (51.79%) at the 100 nmol/L concentraton of NLK siRNA compared to the non-silencing control (Scr, 40.84%).

Based on the above result, the present inventors could confirm that, when NLK expression is inhibited by treating the hepatoma cell line (Hep 3B) with NLK siRNA, G1 phase increases than the control with non-inhibited NLK expression, while S phase is induced to be reduced. This leads into the fact that NLK RNA silencing can be one of the causes that reduce proliferation rate of HCC. Further, it was also recognized that NLK according to the present invention can play a vital role in the G1/S transition in the cell cycle progression of HCC, and that suppression of NLK expression can suppress proliferation of carcinoma cell by inducing delayed G1/S transition.

EXAMPLE 6

Apoptosis Assay of HCC Cell with Inhibited NLK Expression

Furthermore, the present inventors analyzed apoptosis level of Hep3 cell and SNU-423 cell when NLK expression was inhibited. The Annexin V-FITC Apoptosis Detection Kit I (BD Biosciences) was used to quantify the level of apoptosis in the samples. To be specific, the cells were trypsinized, washed twice with cold PBS and resuspended in 1× binding buffer at a concentration of $1 \times 10^6$ cells/ml. The cells were transferred, 100 μl of the cell suspension ($1 \times 10^5$ cells), to a 5 ml culture tube and 5 μl of Annexin V-FITC and 10 μl of PI solution was added. After 15 min of incubation at room temperature in the dark, 400 μl 1× binding buffer was added to each of the culture tubes; determination of the apoptotic fraction of cells was then performed by Cell-Quest FACS analysis software on a FACScan flow cytometer (BD Biosciences). The control was treated with scrambled siRNA instead of NLK siRNA.

Figure 9:
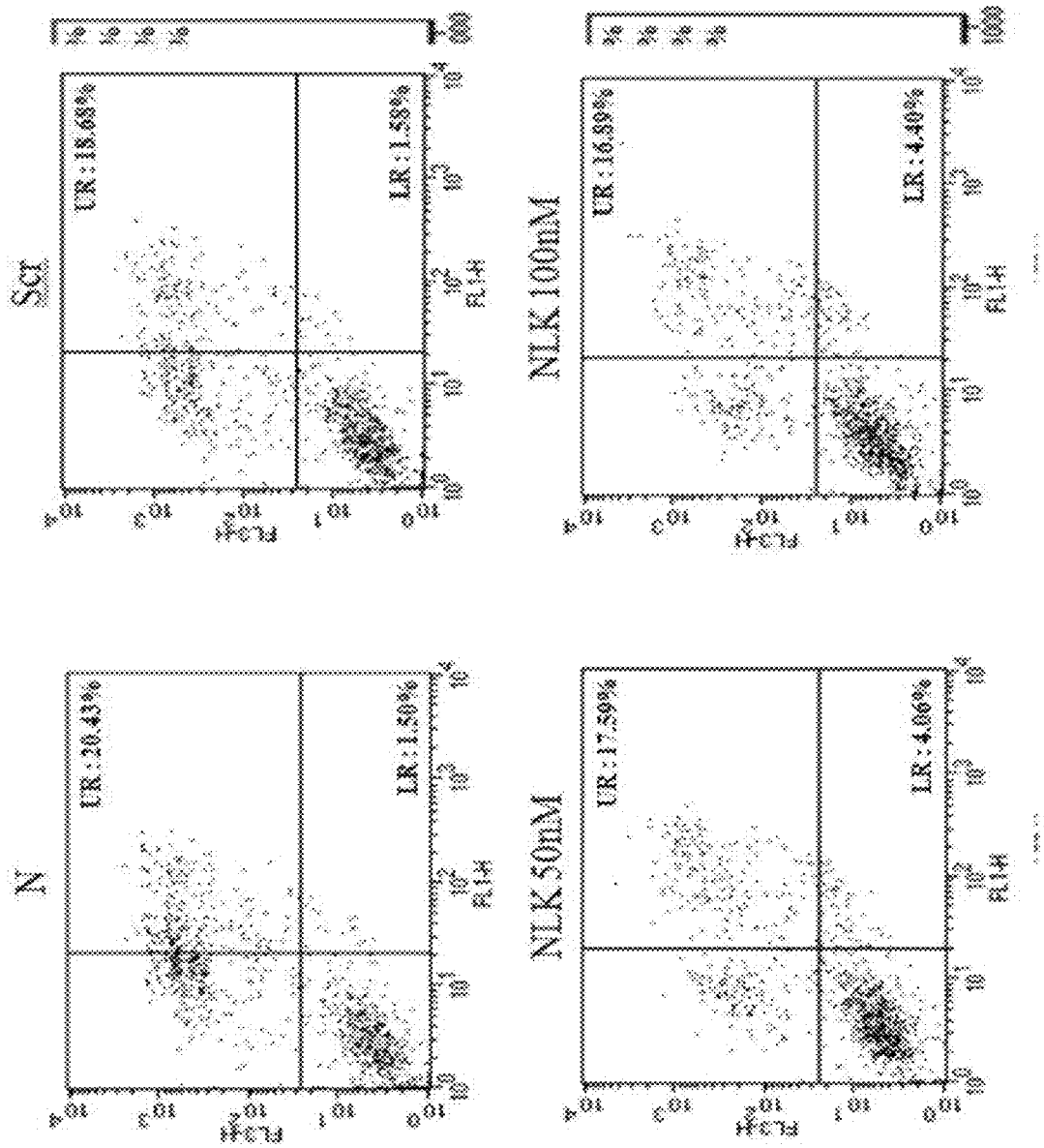
FIG. 9 shows images analyzing apoptosis by Anexin V staining, after inhibiting expression of NLK in He3B cell using NLK siRNA.

As a result, as shown in FIG. 9, the flow cytometry analysis with PI and Annexin V staining, for the dead cells or apoptotic cells, indicated that cellular apoptosis (upper right in dot plot graphs) was not affected by NLK silencing.

These results suggest that the mechanism to prevent or treat liver cancer through inhibition of NLK expression can be performed by causing cell cycle arrest, and not by apoptosis, and that it is possible particularly by inhibiting G1/S cell cycle.

EXAMPLE 7

Effects of NLK on G1/S Cell Cycle Transition

From the above findings, the present inventors were able to confirm that suppression of NLK caused regression of hepatoma cell growth. Accordingly, the inventors examined the effects of the key components in the cell cycle, i.e., CDK (cyclin dependent kinases), CDK inhibitors (CDKIs) and cyclins as follows:

(1) Expression of Cell-Cycle Regulators According to Suppression of NLK

Among the regulators involved in the transition of cell cycle phase from G1 to S, it has been well established that negative cell-cycle regulators such as $p21^{WAF1/CIP1}$, $p15^{INK4B}$ $p16^{INK4A}$ and $p27^{Kip1}$ are the key modulators that suppress cyclin D1/CDK4, 6 or cyclin E/CDK2 complexes. Accordingly, the present inventors examined the effects of the suppression of NLK on the expression of the cell-cycle regulators in the hepatoma cell by the Western blot analysis. The antibodies regarding cell-cycle regulators (p21, p15, p16, p27, Cyclin D1, CDK2) and NLK antibody were purchased from Cell Signaling (Cell Signaling Technology Inc, Beverly, Mass.) and Abcam (Abcam Inc. Cambrige, Mass.). For this measurement, whole-cell extracts were prepared with radio-immunoprecipitation assay (RIPA) lysis buffer (50 mmol/L Tris-HCl, pH7.4, 150 mmol/L NaCl, 1% Nonidet P-40, 0.25% sodium deoxycholate, 1 mmol/L Phenylmethane-sulfonylfluoride containing protease inhibitors, Roche, Mannheim, Germany). Protein concentrations were determined using the BCA protein assay kit (Pierce, Rockford, Ill.) and absorbance of the protein samples were read at 570 nm with the VICTOR3™ Multilabel Plate Reader (PerkinElmer). RIPA lysates containing 10 μg or 15 μg of protein were separated by SDS-PAGE and transferred onto a polyvinylidene difluoride membrane (Amersham Hybond™-P, Little Chalfont, Buckinghamshire, UK) and kept in 5% skim milk (BD Biosciences) in TBS solution containing 0.05% Tween-20 (Usb Corporation, Cleveland, Ohio) overnight to protect against non-specific binding. The membranes were incubated with each of the primary antibodies and horseradish peroxidase (HRP)-conjugated secondary antibodies (Pierce). The ECL plus Western blotting detection system (Amersham) was used to detect immobilized specific antigens conjugated to HRP labeled antibodies. The membrane was exposed to LAS 3000 (Fuji Photo Film Co. LTD, Japan) to measure the amount of expressed protein. Cells transfected with scrambled siRNA was used as the control.

Figure 10:
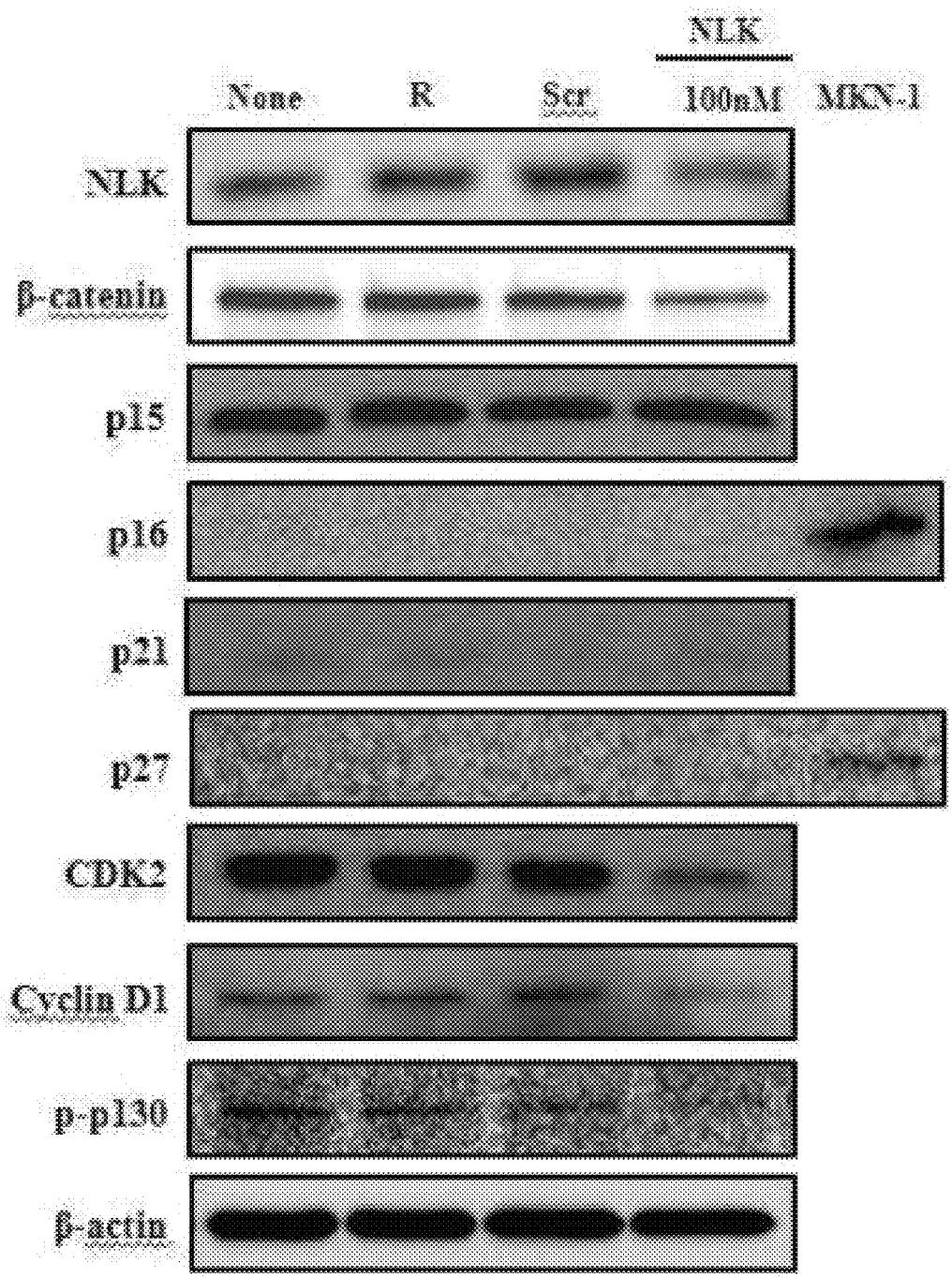
FIG. 10 shows images analyzing expression levels of the cell cycle regulating factors by Western blot analysis, when NLK expression is inhibited in cell using NLK siRNA.

As a result, as shown in FIG. 10, in the cells transfected with NLK siRNA so that NLK is not expressed, cyclins D1 and CDK2 were down-regulated. These result suggests that over-expression of NLK, in HCC cells, might concomitantly activate expression of both cyclin D1 and CDK2.

(2) Phosphorylation of P130, pRb Proteins

Thus, to verify relationship between NLK and CDK2 and cyclin D1 expression, the inventors evaluated phosphorylation status of p130, pRb protein, when NLK was knock-downed in Hep3B cells. The measurement was conducted in the same manner as the Western blot analysis explained above.

As a result, as shown in FIG. 10, disruption of NLK expression elicited hypo-phosphorylation of p130, implying aberrant regulation of NLK affects phosphorylation of pRb protein family via transcriptional activation of CDK2 and cyclin D1 in HCCs.

This also suggests that simultaneous regulation of CDK2 and cyclin D1 by NLK exerts very potent mitogenic stimulation causing uncontrolled cell growth during liver cancer progression.

(3) Suppression of β-Catenin

The present inventors also confirmed through the above tests the effects of suppression of NLK in Hep3B cell on the expression of β-catenin.

As a result, as shown in FIG. 10, it was observed that the expression of β-catenin is suppressed in the cells where the NLK is suppressed.

The above findings suggest another possible mechanism of NLK that regulates β-catenin stability in Hep3B cells, and therefore, despite the previous studies that report that NLK negatively regulate Wnt signaling through phosphorylation of the T cell factor/lymphoid promoter, the above findings elucidated another NLK mechanism that is distinct from the previously reported one.

EXAMPLE 8

Suppression of Proliferation of Liver Cancer Cell according to Suppression of NLK Finally, the prevent inventors conducted Soft-agar colony formation assay to verify if suppression of NLK can inhibit the proliferation of the liver cancer and eventually prevent or treat the liver cancer. To this purpose, forty-eight hours after transfection with NLK siRNA, ~5,000 cells in 1 ml of 0.4% agarose with RPMI-1640 were plated in each well on the top of existing 0.8% bottom agarose in 35 mm dishes in triplicate for each treatment condition. The plates were covered with 500 μl of medium with 10% FBS and incubated at 37° C. in a 5% $CO_2$ incubator for 3 weeks. The covering medium was replaced every week. At the end of 3 weeks, cell colonies were stained with 0.05% crystal violet and colonies>0.1 mm in diameter were counted under a microscopic field at x40 magnifications. Means were based on numbers from triplicate wells for each treatment condition and were analyzed using one-sided Student's t test.

As a result, as shown in FIG. 11, knock-down of NLK resulted in the reduction of colony formation number compared to corresponding controls.

The above results suggest that targeted-disruption of NLK in liver cancer cell or tissue suppressed proliferation of cancer cells and induces reduction of anchorage-independent growth, thereby providing effect of preventing or treating liver cancer.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for treating liver cancer, comprising administering siRNA, having a sequence of SEQ ID NO: 2 or SEQ ID NO: 3, for inhibiting expression of nemo-like kinase (NLK) to a subject in need of the same.

2. The method as set forth in claim 1, wherein the liver cancer is hepatocellular carcinoma (HCC).

3. A kit for diagnosis of liver cancer by RT-PCR, comprising an RT-PCR primer having a sequence of SEQ ID NO: 4 or SEQ ID NO: 5.

4. The kit as set forth in claim 3, further comprising an RT-PCR primer having a sequence of SEQ ID NO: 6 or SEQ ID NO: 7.

* * * * *